US012642661B2

(12) United States Patent
Caiazza

(10) Patent No.: US 12,642,661 B2
(45) Date of Patent: Jun. 2, 2026

(54) ADJUSTABLE MOLD FOR FORMING SPACER DEVICES OR PARTS THEREOF

(71) Applicant: Tecres S.p.A., Sommacampagna (IT)

(72) Inventor: Emanuele Caiazza, Rome (IT)

( * ) Notice: Subject to any disclaimer, the term of this patent is extended or adjusted under 35 U.S.C. 154(b) by 136 days.

(21) Appl. No.: 18/554,853

(22) PCT Filed: Apr. 16, 2022

(86) PCT No.: PCT/IB2022/053587
§ 371 (c)(1),
(2) Date: Oct. 11, 2023

(87) PCT Pub. No.: WO2022/224117
PCT Pub. Date: Oct. 27, 2022

(65) Prior Publication Data
US 2024/0180709 A1      Jun. 6, 2024

(30) Foreign Application Priority Data
Apr. 19, 2021     (IT) ........................ 102021000009908

(51) Int. Cl.
*A61F 2/30*          (2006.01)
*A61F 2/38*          (2006.01)
(52) U.S. Cl.
CPC ........ *A61F 2/30942* (2013.01); *A61F 2/3859* (2013.01); *A61F 2/389* (2013.01); *A61F*
2002/30616 (2013.01); *A61F 2002/30957* (2013.01); *A61F 2310/00353* (2013.01)
(58) Field of Classification Search
CPC .... A61F 2/30942; A61F 2/3859; A61F 2/389; A61F 2002/30616; A61F 2002/30957; A61F 2310/00353; A61F 2/38; A61F 2002/30556; A61F 2/3094; A61F 2002/30537; B29C 33/308; B29C 33/12
See application file for complete search history.

(56) References Cited

U.S. PATENT DOCUMENTS

| | | | |
|---|---|---|---|
| 9,433,506 B2 | 9/2016 | Lomicka et al. | |
| 2015/0061181 A1 | 3/2015 | Haney | |
| 2022/0015911 A1* | 1/2022 | Vogt | ......................... A61F 2/32 |
| 2022/0151790 A1* | 5/2022 | Hay | ..................... A61F 2/3859 |

FOREIGN PATENT DOCUMENTS

| | | |
|---|---|---|
| WO | 2018227267 | 12/2018 |

* cited by examiner

*Primary Examiner* — S. Behrooz Ghorishi
(74) *Attorney, Agent, or Firm* — Themis Law

(57) ABSTRACT

An adjustable mold for forming spacer devices or parts thereof for the replacement of a joint prosthesis or part thereof, and the related kit for forming such spacer devices or parts thereof.

17 Claims, 9 Drawing Sheets

SD1

1

SD1

1

1

ADJUSTABLE MOLD FOR FORMING SPACER DEVICES OR PARTS THEREOF

TECHNICAL FIELD OF THE INVENTION

The present invention relates to an adjustable mold for forming spacer devices or parts thereof for the replacement of a joint prosthesis or of a part thereof and the relative kit for forming such spacer devices or parts thereof. The present invention also relates to a method of forming a spacer device through the aforementioned adjustable mold as well as a kit for forming spacer devices or parts thereof.

STATE OF THE ART

The material with which spacer devices for replacing a joint prosthesis are usually made is a known material, for example bone cement, which initially appears in the fluid state and which, after a certain period of time, hardens. This material, once hardened, constitutes the structure of the spacer device.

The shaping process of the spacer device itself usually takes place through the use of special molds, which can be used directly by the surgeon in the operating room, or even at external production sites, which are then responsible for providing the surgeon, who must perform the implant, a pre-formed spacer device substantially ready for being used.

In the first case, doctors often use flexible molds that fill with bone cement in a fluid state and from which, after the bone cement has solidified, they extract the formed spacer device by elastic deformation or not.

Such spacer devices often have to be made and adapted to the physical conformation and needs of each patient, thus resulting in a great burden for designing the molds.

In fact, it often happens that different patients need spacing devices with different heights, thicknesses or in any case measures one from the other.

This forces the surgeon to use different molds to obtain the spacer device suitable for the particular needs of the client.

There is therefore a need to have a new type of adjustable mold for forming spacer devices or parts thereof for the replacement of a joint prosthesis or a part thereof that overcomes the drawbacks of the known art.

OBJECTS OF THE INVENTION

The main object, therefore, of the present invention is to improve the state of the art in the field of molds for forming spacer devices for replacing a joint prosthesis or part thereof.

Another object of the present invention is to provide a mold for forming spacer devices which is quick and easy to use.

Another object of the present invention is to provide a mold for forming spacer devices which is highly versatile.

Yet another object of the present invention is to provide a mold for forming spacer devices, which can obtained at competitive costs.

A further object of the present invention is to provide a mold for forming spacer devices that allows the latter to be made in a number of sizes, for example in various heights or thicknesses, thereby making it adaptable to the different needs of each patient.

According to an aspect of the present invention, a mold for forming spacer devices or parts thereof according to claim 1 is provided.

Subject-matter of the present invention is also a kit for forming spacer devices or parts thereof according to claim 12.

According to another aspect of the present invention, a method for forming a spacer device or a part thereof according to claim 14 is also provided.

The dependent claims refer to preferred and advantageous forms of the invention.

BRIEF DESCRIPTION OF THE DRAWINGS

Further characteristics and advantages of the present invention will become more evident from the detailed description of some preferred embodiments of an adjustable mold for forming spacer devices or parts thereof, illustrated by way of non-limiting example, in the accompanying drawings in which.

In the accompanying drawings, identical parts or components are indicated by the same reference numbers.

EMBODIMENTS OF THE INVENTION

Figures 1, 2, 3:
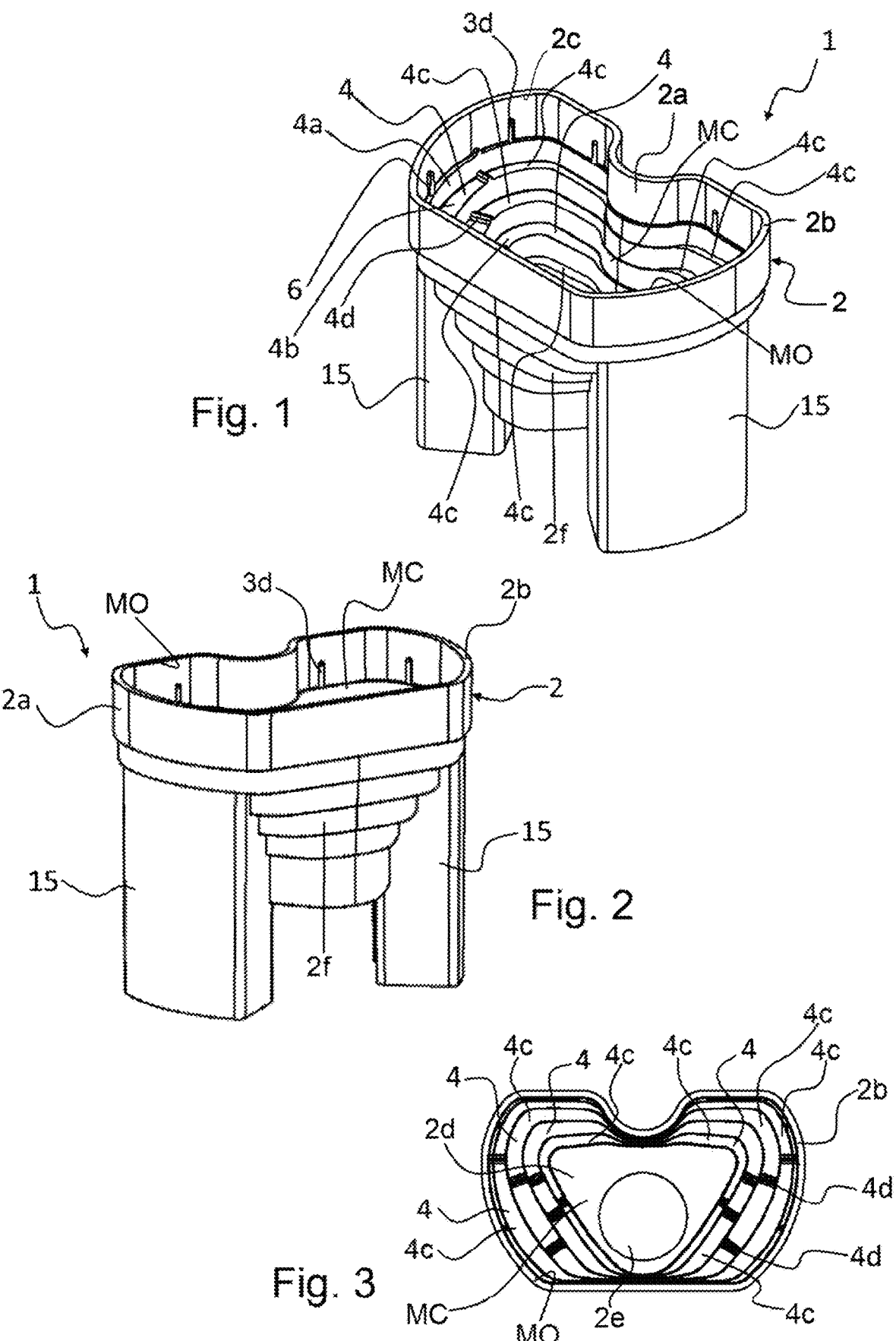
FIGS. 1 and 2 show two perspective views of an adjustable mold for forming spacer devices or parts thereof according to a version of the present invention.
FIG. 3 illustrates a top view of the mold of FIG. 1.

The present invention refers to an adjustable mold for obtaining or forming spacer devices or in any case of parts thereof for the replacement of a joint prosthesis or anyway of a part thereof.

As it is known, the spacer device is a temporary and disposable device, which is implanted in the human body, for example at a joint prosthesis, for replacing a permanent joint prosthesis. This occurs substantially because the implantation site of the permanent joint prosthesis undergoes an infection and it is necessary, on the one hand, to treat this infection after the infected prosthesis has been removed and, on the other hand, to maintain the joint space until the implantation of a new prosthesis in the surgical site from which the infection was eradicated.

These functions are performed by the spacer device, which is made of a suitable biocompatible material, such as a bone cement with an acrylic resin base, for example polymethylmethacrylate, which has been added with at least one medical substance with an antimicrobial action, for example an antibiotic. The most commonly used antibiotics are one of gentamicin, vancomycin, or combinations thereof.

With reference to the attached figures, the mold 1 can be used for obtaining or forming spacer devices or in any case of parts thereof. The mold 1 is particularly suitable for obtaining or forming spacer devices suitable for being implanted, in use, at the tibial bone of the knee joint, but in other versions of the invention they could also be used for forming spacer devices or parts thereof suitable for being implanted, in use, in other bone sites, for example at the femoral bone of the knee joint, at the femoral bone of the hip joint or even at the humeral and/or clavicular and/or scapular bone of the shoulder joint.

In general, the mold 1 comprises at least one main body 2 and defines a molding cavity MC.

The mold 1 also includes means for adjusting 3 the height of the at least one molding cavity MC delimited by the main body 2 and/or by the adjusting means or, alternatively or in addition to the adjusting means, reference means 3 for the controlled filling of the at least one molding cavity MC are provided, so that it is possible to vary the height of the at least one molding cavity MC or to carry out a controlled filling of the same in such a way that the mold 1 allows to form at least two spacer devices SD with different heights or thicknesses with respect to each other.

The main body 2 is preferably a rigid structure, i.e., it does not deform when subjected to the reaction forces that are developed during the forming reaction of the spacer device SD now being discussed and can be made of any biologically compatible material, such as for example ceramic or plastic or other.

As relates to the plastic, it can comprise at least one thermoplastic polymer, an acrylic resin, an acrylic polymer and/or copolymer, polymethyl methacrylate, a bone cement comprising polymethyl methacrylate and/or a similar polymer.

On the other hand, as regards ceramics, the material can comprise a ceramic bone cement, optionally comprising calcium sulphate ($CaSO_4$), or other components containing calcium.

In an alternative version of the invention, the main body 2 can be made of a biologically compatible plastic and/or polymeric material such as for example polyethylene or high-density polyethylene or ultra-high molecular weight polyethylene (UHMWPE).

According to the version of the invention shown in FIGS. 1 to 15, the main body 2 has a configuration such as to define a molding cavity MC. More specifically, the main body 2 can comprise at least one base component 2a with an open concave or box-like configuration so as to define a cavity which, together with or thanks to the adjusting means 3, defines the molding cavity MC.

Said molding cavity MC can be, for example, substantially conical, frustoconical or pyramidal, if desired, inverse pyramidal or inverse truncated pyramid. This conformation of the main body 2 of the mold 1 has the function of providing the spacer device SD or a part thereof, obtained with this mold 1, with a configuration suitable for making a tibial spacer device easily adaptable to the respective implant site.

In this regard, according to the embodiment illustrated in the figures, the base component 2a includes a bottom wall 2d and a side wall 2f, for example annular or cylindrical or with a regular or irregular closed configuration protruding from the bottom wall 2d, if desired from the outer edge of the same. The cavity where the molding cavity MC can be identified, is defined between the base wall 2a and the side wall 2f.

In other versions of the invention, the conformation of the main body 2 could also be different, based on the particular conformation needs of the spacer device SD or in any case according to the type of mold 1 used.

Advantageously, the adjusting means 3 can comprise at least one auxiliary or lateral component or insert 3a which can be engaged or otherwise connected to the base component 2a and which is designed to define or delimit the bottom and/or the top of the at least one molding cavity MC. This at least one auxiliary or lateral component or insert 3a allows, in fact, to define or delimit the height or thickness of each spacer device SD or of a part thereof, which will be formed through the mold 1 or, better, through the at least one molding cavity MC.

In particular, the at least one base component 2a or the at least one auxiliary or lateral component or insert 3a or better the internal, in use, surface of the at least one base component 2a or the internal surface, in use, of the at least one auxiliary or lateral component or insert 3a, can comprise one or more defining or delimiting sections 4 designed to define or delimit the surface or lateral extension of the at least one molding cavity MC. Actually, these one or more defining or delimiting sections 4 define or delimit the external surface or structure of each spacer device SD, or of a part thereof, which will be formed through the mold 1 or, better, through the at least one molding cavity MC.

The one or more defining or delimiting sections 4, for example according to the embodiment of FIGS. 1 to 15, can be defined by the main body 2 or better by the base component 2a. This allows to obtain a well-defined molding cavity MC, eliminating the possibility that, during the forming phase, the material used for the realization of the spacer device SD or of a part thereof, can infiltrate between possible joints, for example, of the at least one auxiliary or lateral component or insert 3a.

In other versions of the invention (see for example FIGS. 16 to 19), the one or more defining or delimiting sections 4 can be defined by auxiliary or lateral components or inserts of the adjusting means 3 which can be inserted in the main body 2, if desired in the base component 2a or above it, to delimit the at least one molding cavity MC.

If desired, the defining or delimiting sections 4 delimit at least one contact or abutment surface 4c for an insert 3a.

Preferably, the defining or delimiting sections 4 delimit a plurality of contact or abutment surfaces 4c for one or more inserts 3a, each contact or abutment surface 4c being at a respective height of the molding cavity MC.

The contact or abutment surfaces 4c can be, for example, annular, with a circular, rectangular or even irregular outer and inner perimeter.

Advantageously, the defining or delimiting sections 4 delimit a molding cavity MC configured in a stepped manner.

Basically, at least one defining or delimiting section 4 includes at least a first section 4a and at least a second section 4b consecutive to each other, i.e., having at least one end in common.

In at least one version of the invention, the at least one first section 4a and the at least one second section 4b can be perpendicular to each other, thus providing at least one defining or delimiting section 4, preferably each defining or delimiting section 4 with a step configuration or in any case with a configuration delimiting at least one shoulder. These configurations of the one or more defining or delimiting sections 4 allow to define or delimit a contact or abutment surface 4c for the insert 3a, preferably a plurality of contact or abutment surfaces 4c for inserting and supporting each at least one respective insert 3a. According to the embodiment illustrated in the figures, the contact or abutment surface 4c may correspond to one of the aforementioned sections 4b.

Naturally, the main body 2 defines, at one end 2c, a main opening MO for accessing to the molding cavity MC. The main opening MO is delimited by an external free edge 2b of the main body 2.

If desired, the main body 2 or, better, the base component 2*a* comprises at least a bottom 2*d* opposite the main opening MO. The bottom 2*d* could be open so as to define a light or through opening 2*e* or, alternatively, could also be closed.

In particular, the internal, in use, surface of the base component 2*a* defines the one or more defining or delimiting sections 4, which, in turn, define at least one contact or abutment surface 4*c* each for a respective insert 3*a*.

According to the non-limiting embodiment illustrated in FIGS. 1 to 15, the section of the molding cavity MC decreases, for example in steps or also according to another pattern starting from the main opening MO, towards the inside or the bottom of main body 2.

Still in accordance with the non-limiting embodiment shown in FIGS. 1 to 15, the adjusting means 3 comprise at least one insert 3*a*, preferably a plurality of inserts 3*a*, which can be inserted into the main opening MO for accessing the molding cavity MC until it abuts against a respective contact or abutment surface 4*c*.

Clearly, according to this variant, the mold 1 comprises a single insert 3*a* which is selected from a plurality of inserts 3*a* and inserted for defining or delimiting in the molding cavity MC.

This at least one insert 3*a* is preferably a removable and insertable insert, for example to size in the cavity delimited by the main body 2 so that, once abutting against the surface 4*c* it defines the bottom of the molding cavity MC, in fact, by adjusting the height or thickness of the spacer device SD, or of a part thereof, that will be formed. In this case, the molding cavity MC is defined laterally by the internal surface of the main body 2 or, better, of the base component 2*a* and at the bottom by an insert 3*a*.

Figure 4:
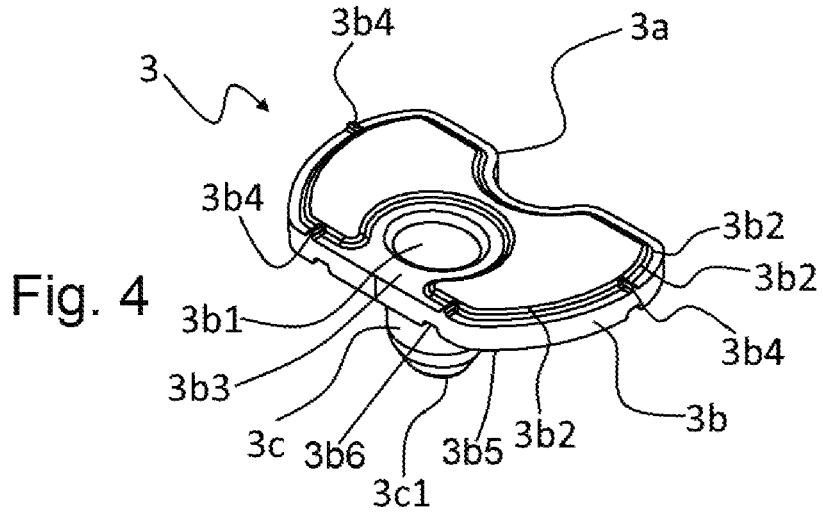
FIGS. 4 and 5 are, respectively, a perspective view and a top view of an adjustment means for the mold of FIG. 1.
Figure 5:
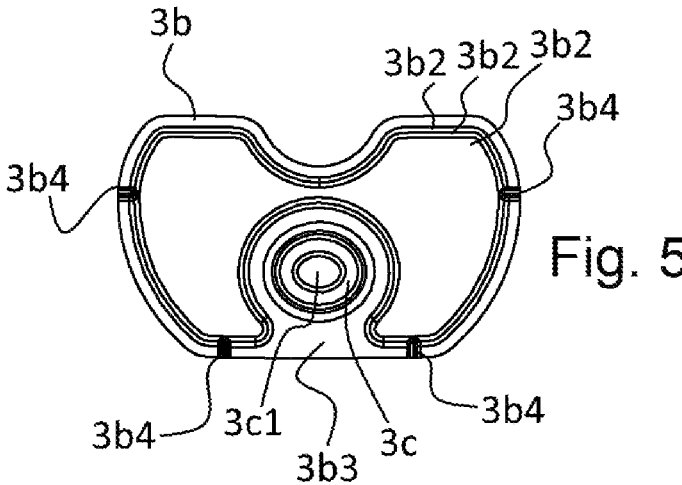

More specifically, according to the exemplary and non-limiting version of the invention shown in FIGS. 4 and 5, the at least one insert 3*a* can comprise at least one base 3*b* and, preferably, also a hollow stem 3*c* rising from the base 3*b*. In this case, the base 3*b* defines an opening 3*b*1 that opens into the hollow stem 3*c* in such a way as to allow the deposition of the material for forming the spacer device SD also in the hollow stem 3*c* once the insert 3*a* has been placed in or on the main body 2.

The base 3*b* can be configured as a plate shaped, for example, as a C. The base 3*b* can have a section much larger than the stem 3*c*.

The base 3*b* can also comprise, on the surface, in use, distal 3*b*3 from the stem 3*c*, at least a raised portion 3*b*2, if desired with an annular edge with one, two, three or more steps.

On the base 3*b* or, better, still on the surface, in use, distal 3*b*3 from the stem 3*c*, can be provided one or more protrusions 3*b*4 designed to determine, in the bottom of the spacer device SD or in a part thereof, obtained through the mold 1, respective grooves or recesses, so as to provide grip points for the device SD with the cement or biocompatible material used for implantation of the spacer device SD in the bone site of a patient. The protrusions 3*b*4 can extend from the raised portion 3*b*2.

Moreover, the hollow stem 3*c* can comprise an end 3*d*1, in use, distal from the base 3*a*, which is preferably rounded, so that this end 3*d*1 can be pressed during the extraction step with the aim of facilitating the expulsion or in any case the separation of the spacer device SD or a part thereof from the mold 1.

In this case, the width of the light or through opening 2*e* is such that, once the at least one insert 3*a* has been inserted into the main access opening MO for the molding cavity MC until it abuts against a respective contact or abutment surface

4*c*, the hollow stem 3*c* or at least the end 3*d*1 thereof can pass or protrude, at least partially, into the light or through opening 2*e*. This configuration makes it possible to facilitate the extraction of the spacer device SD or a part thereof, allowing the surgeon or the user to press the end 3*d*1 of the hollow stem 3*c* protruding through or reaching the light or through opening 2*e* so as to easily detach the spacer device SD or a part thereof from the mold 1 or at least from the main body 2 or from the base component 2*a* thereof.

One or more protrusions or projecting parts 4*d* can then be provided at the defining or delimiting sections 4. The protrusions or projecting parts 4*d* can be provided on the contact or abutment surfaces 4*c*, for example more protruding 4*d* spaced from each other.

These protrusions or projecting parts 4*d* are designed to obtain in the spacer device SD or in a part thereof, obtained through the mold 1, respective hollows or recesses, so as to provide gripping points for the device SD with the cement or material biocompatible used for implantation of the spacer device SD into a patient's bone site.

In this case, in the insert 3*a* or, better, starting from the surface, in use, proximal to the stem 3*c* of the base 3*b*, one or more grooves 3*b*6 are provided designed to engage and house respective protrusions or projecting parts 4*d* on a respective contact or abutment surface 4*c*.

Moreover, the main body 2 or, better, the base component 2*a* can also comprise one or more reference projections or recesses or notches 3*d* (reference means 3) to signal the maximum level of material, for forming the spacer device SD or of a part thereof, with which material the mold 1 or, better, the at least one molding cavity MC can be filled.

These reference projections or recesses 3*d* can extend from one contact or abutment surface 4*c* towards the outside or rather towards the end 2*c* defining the main opening MO. The reference projections or recesses 3*d* may preferably extend from the contact or abutment surface 4*c* closest to the main opening MO.

The main body 2 can then comprise support or prop means 15 to facilitate the support of the mold 1 during the forming operations of the spacer device SD or a part thereof. Said support or prop means 15 are preferably irremovably connected with the main body 2 or better with the base component 2*a* of the mold 1, clearly in an area outside the cavity delimited by the base component 2*a* which, once the at least one auxiliary or lateral component or insert 3*a* has been engaged or inserted, defines the molding cavity MC.

According to the illustrative non-limiting embodiment of FIGS. 1 to 15, for example, two support or prop elements 15 may be provided, such as two leg elements.

For shaping of a complete spacer device SD, i.e. which can be used immediately for being implanted in the patient's bone site, the mold 1 can advantageously be associated with at least one closure element SD1 of the top of the molding cavity MC.

Such at least one closure element SD1 is preferably a component of a spacer device SD.

Alternatively, the closure element is a cover of the molding cavity MC.

The closure element SD1 can be applied and/or can be abutted on the upper, in use, surface of the material previously placed and/or cast in the at least one molding cavity MC of the mold 1 in such a way as to constitute a single body with the material in the at least one molding cavity MC, as the cures.

Alternatively, a component SD1 of the spacer device can be connected to a part of the latter obtained in the mold 1 after this part has been obtained and extracted. Such a connection could be made for example by means of bone cement.

Figure 6:
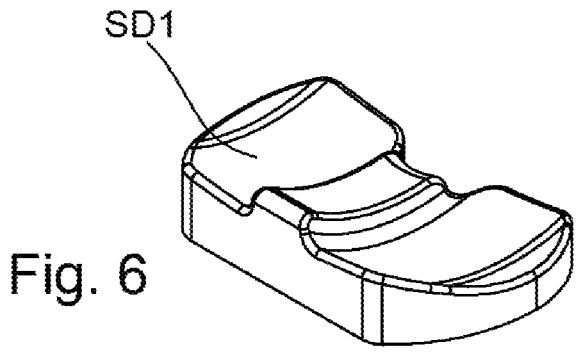
FIG. 6 shows a closure element for the mold of FIG. 1.
Figure 7:
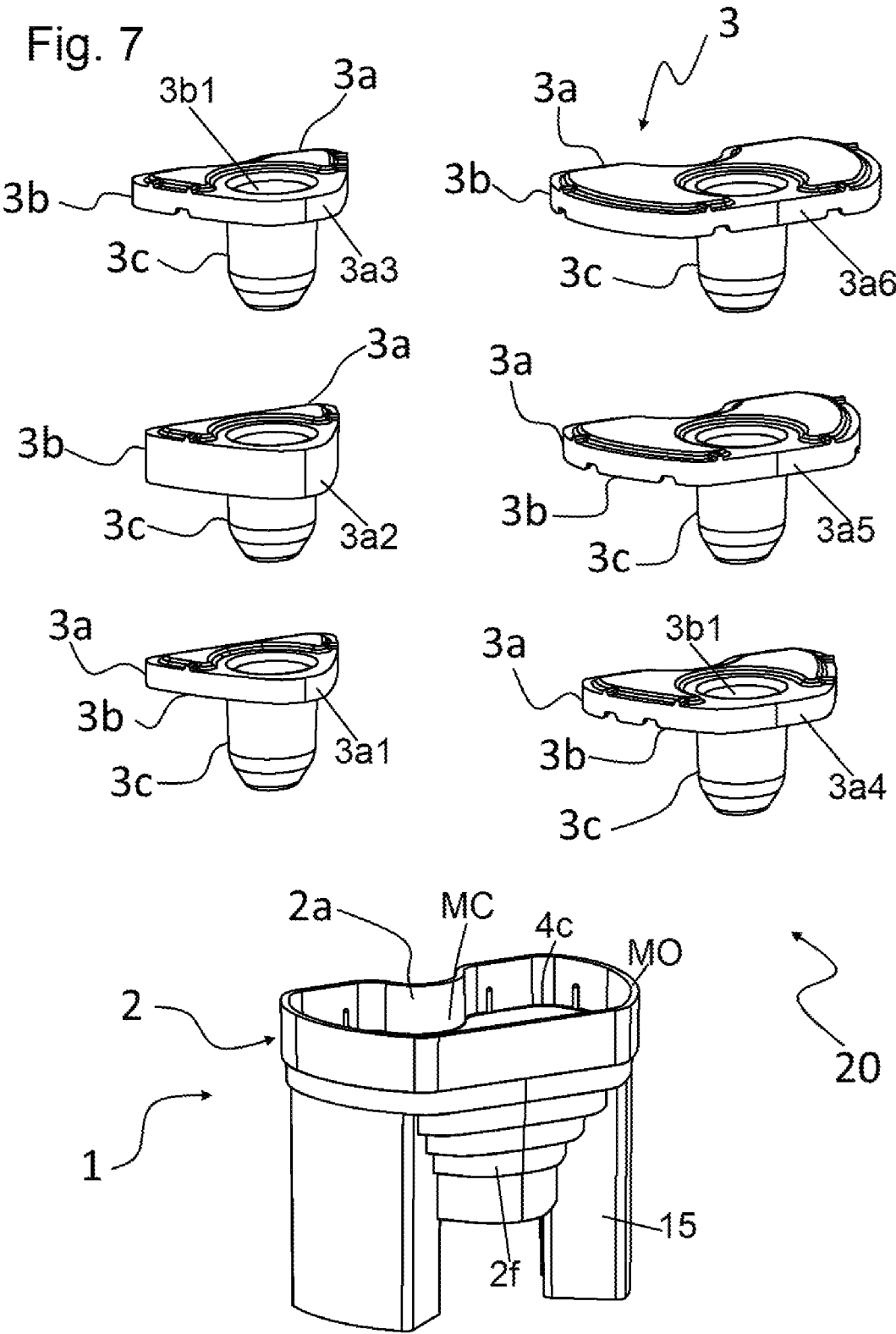
FIG. 7 shows a kit for forming spacer devices or parts thereof according to a version of the present invention.

FIG. 6 shows a possible closure element SD1 which actually constitutes the tibial plate for a tibial spacer device SD to be formed by means of the mold.

The present invention also relates to a kit 20 for forming at least two spacer devices SD or parts thereof for replacing a joint prosthesis or part thereof. This kit 20 comprises at least one mold 1 and at least two auxiliary or lateral components or inserts 3a.

More specifically, the two auxiliary or lateral components or inserts 3a have different dimensions from each other so as to determine the formation of spacer devices with different thickness or height.

In the exemplary and non-limiting version of the kit 20 shown in FIG. 3, there are six inserts 3a each having a dimension such that it can be brought into abutment against a respective contact or abutment surface 4c. More particularly, according to the embodiment in the figures, the inserts 3a each have a base 3b with a width and, if desired, also a thickness different from the other inserts, so that each insert 3a can be abutted against a respective contact or abutment surface 4c different from the others.

In practice, each insert 3a is associated with a determined height or thickness which is to be obtained for a spacer device SD or a part thereof. Thus, for example, if a first insert 3a is used having a base with a section larger than a second insert 3a, it is possible to decrease the height or thickness of the spacer device SD, or of a part thereof or vice versa. In this regard, if a first insert 3a6 that is placed has size greater, with particular reference to the respective bases 3b, than another or second insert 3al, considering that the molding cavity MC has preferably size decreasing towards the inside, the first insert 3a6 will abut against an outermost shoulder or closer to the inlet or top of the molding cavity MC, so that by using the first insert 3a6 a molding cavity MC will be obtained having a height less than the case where a second insert 3al with smaller dimensions or width of the respective base 3b is used.

Naturally, the height of the molding cavity MC is defined between the insert 3a and the main opening MO for accessing the molding cavity MC, although this cavity could also, in use, not be completely filled, but only up to a certain height, if desired, identifiable thanks to the reference projections or recesses or notches 3d.

Owing to six inserts 3al-3a6 and to a base component 2a configured as indicated above, it is possible to obtain six spacer devices SD with different heights or thicknesses from each other, so if one switches from a insert 3al with a minimum base 3b (first on the left and at the bottom in FIG. 7) up to an insert 3a6 with maximum base 3b (first on the right and at the top in FIG. 7), molding cavities MC will be obtained gradually with a lower height.

The kit 20 is naturally associated with at least one closure element SD1 which, in use, can be placed on top of the material MM cast or placed in the molding cavity MC or on a contact or abutment surface 4c or on the external free edge 2b.

The present invention also relates to a method for obtaining or forming a spacer device SD or a part thereof, for example as shown in FIGS. 8 to 15.

This method initially comprises the step of providing a mold 1 or a kit 20.

Subsequently, there is the step of defining or delimiting the desired height or thickness of the spacer device SD or anyway of a part thereof by adjusting and/or reference means 3.

Figures 8, 9, 10:
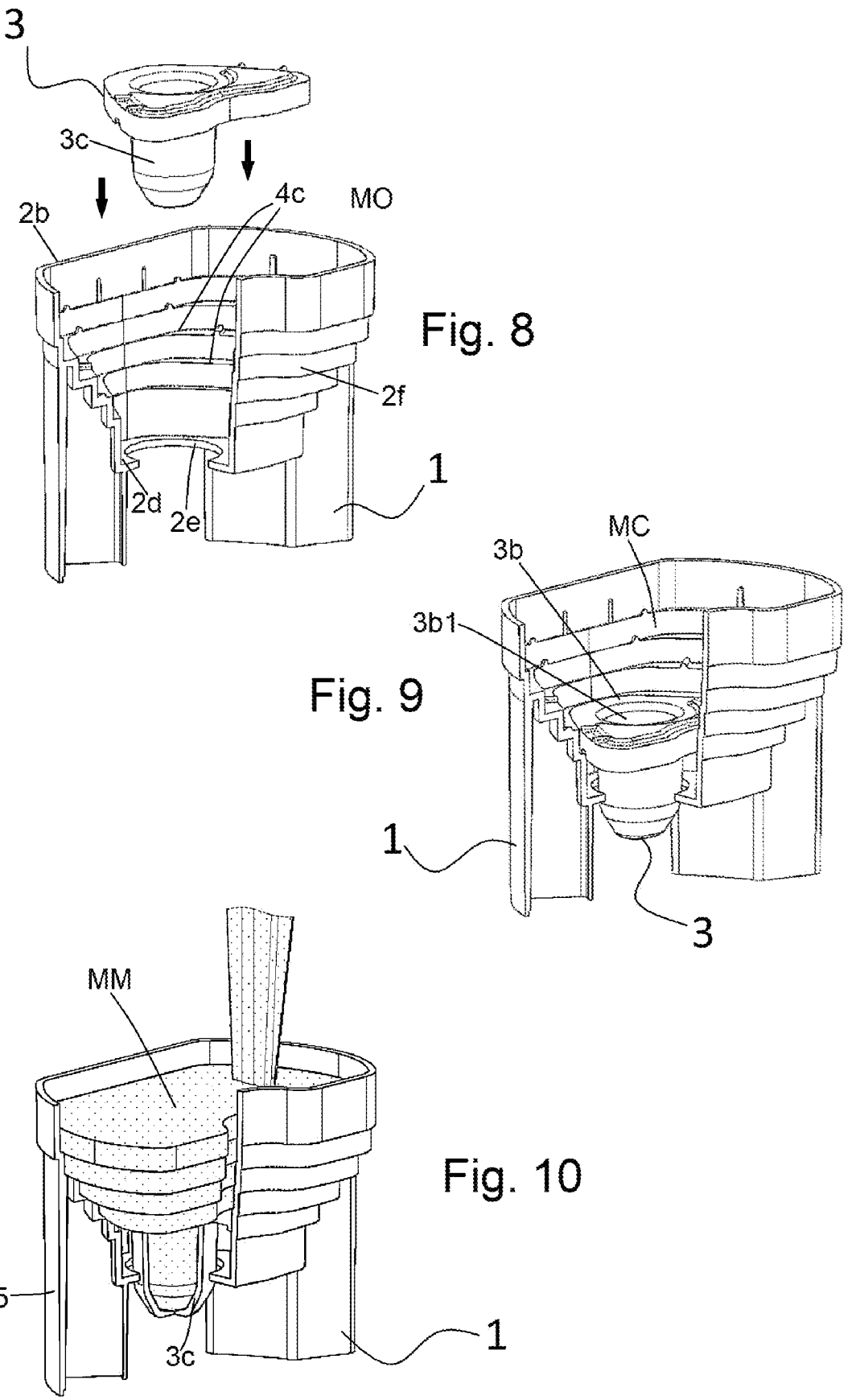
FIGS. 8 to 15 show the steps of a method for forming a spacer device or a part thereof using the mold of FIG. 1.
Figures 11, 12, 13:
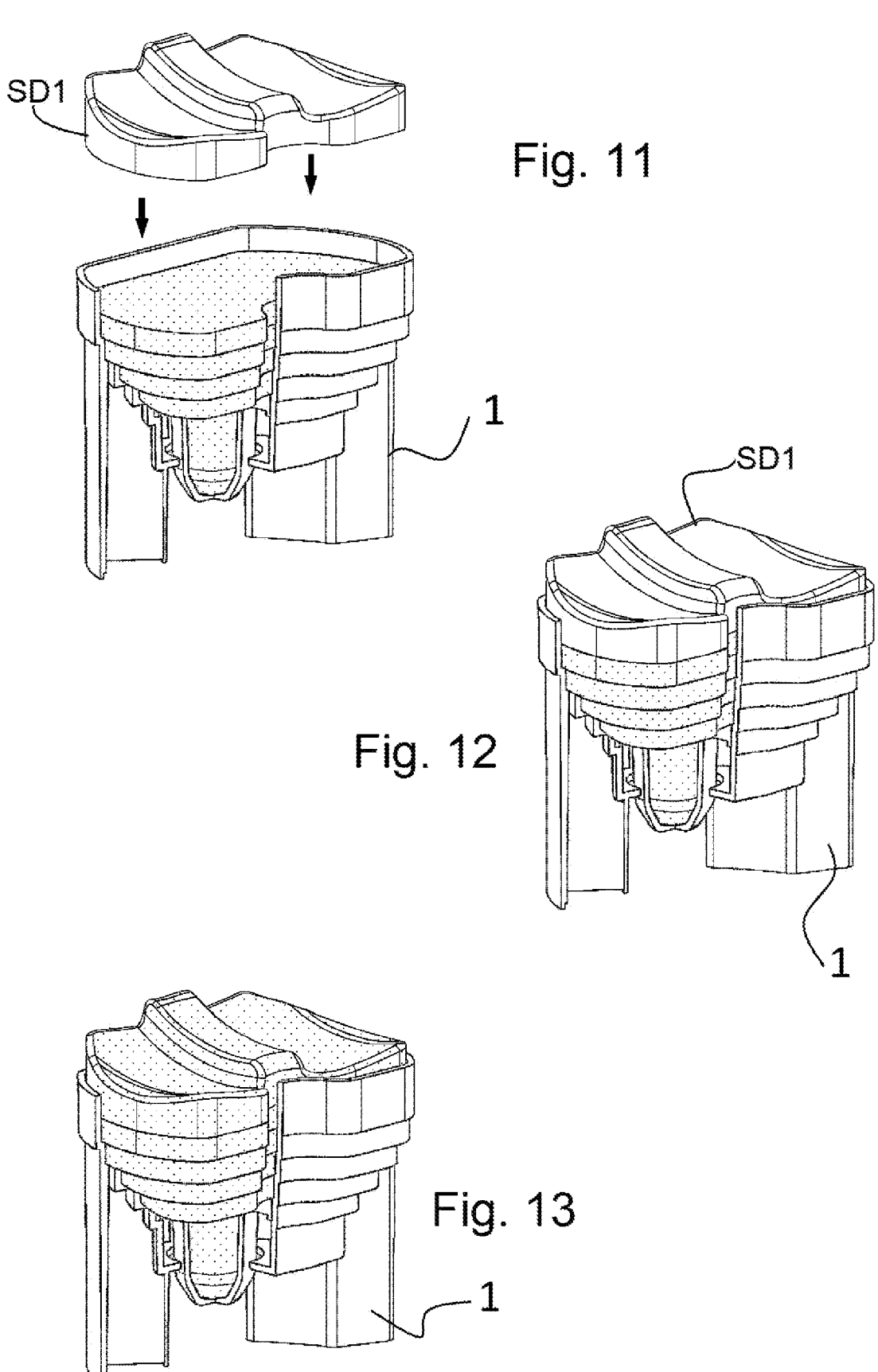
Figures 14, 15:
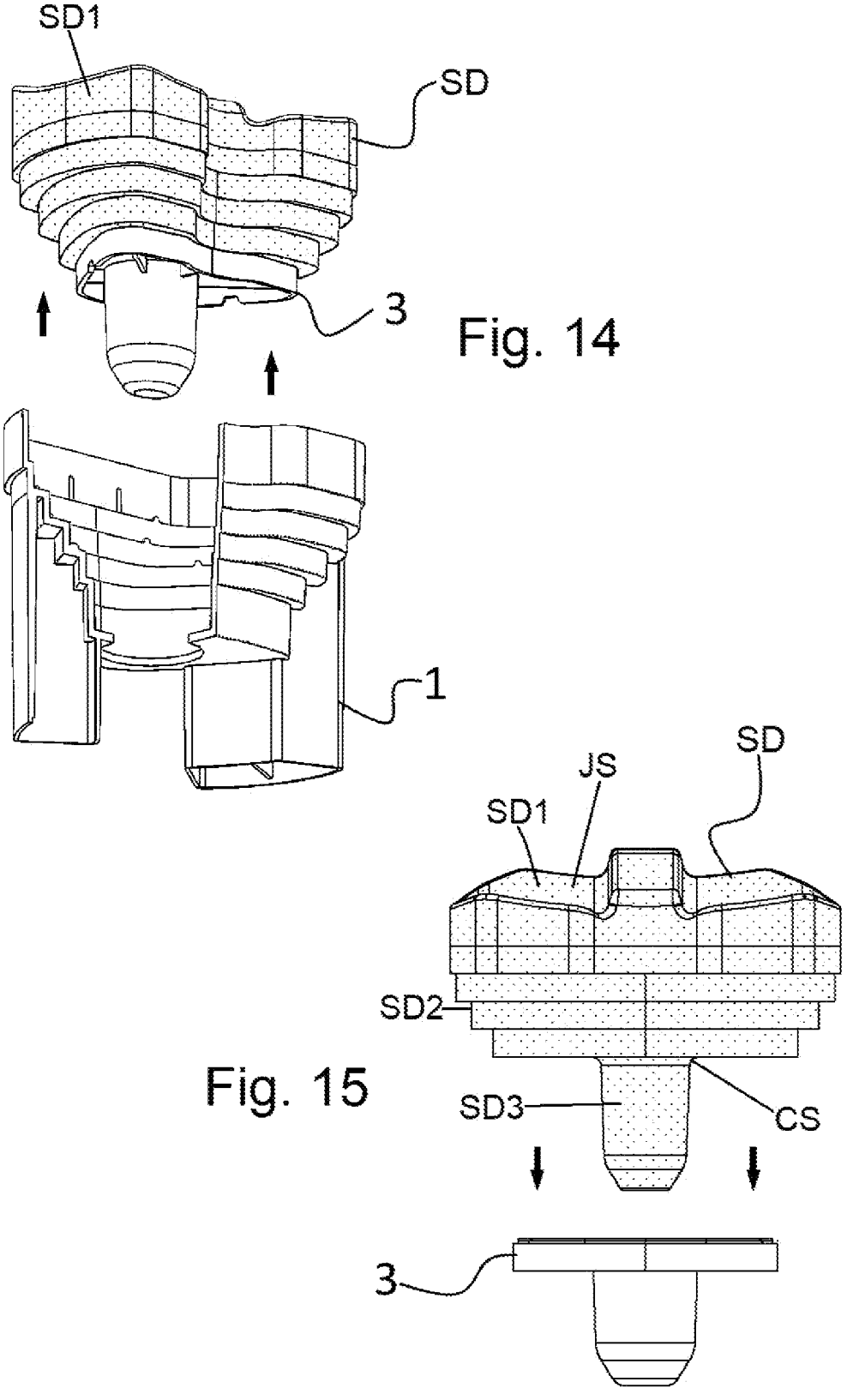

This step of defining or delimiting can comprise the sub-step of inserting at least one insert 3a until it abuts against a contact or abutment surface 4c so as to constitute, with the at least one insert 3a, the bottom 2d of the molding cavity MC (see FIGS. 8 and 9).

Subsequently or even previously, the step of providing at least one material for manufacturing the spacer device SD or a part thereof is envisaged. This material can be of the types described above.

Subsequently, the step of placing and/or casting (see FIG. 10) such material MM in the at least one molding cavity MC of the mold 1 or better of the main body 2 is foreseen up to a height or thickness of the spacer device SD or of a part thereof, for example previously defined or delimited by the adjusting or reference means 3. Basically, according to the embodiment of FIGS. 1 to 15, the material MM cast or placed in the molding cavity MC starting from the main opening MO fills the molding cavity MC defined below by the insert 3a, which in this case defines the bottom 2d of the molding cavity MC. However, if the insert 3a further includes a hollow stem 3c, the material MM also fills the cavity within the latter.

The filling top of the molding cavity MC can instead be established by the surgeon or operator, if desired by referring to the reference projections or recesses or notches 3d.

Finally, the step is provided of waiting for a time for the polymerization and/or hardening of the material and forming the spacer device SD or a part thereof.

The method can also provide, for example before the waiting step, the step of applying or abutting at least one closure element SD1 on an upper, in use, surface of the material previously placed and/or cast in the mold 1 or better in the at least one molding cavity MC, so that the closure element SD1 constitutes the top of the spacer device SD. The next step of waiting will make it possible the polymerization and/or hardening of the material placed or cast with the closure element SD1, thereby making it possible to obtain a spacer device SD in a single piece. Alternatively, the closure element SD1, such as a tibial plate, can be applied or connected, if desired by bone cement, on the part of the spacer device obtained in the mold, after that this part has been extracted from the mold itself.

Furthermore, the forming method can then comprise the step of extracting the spacer device SD or a part thereof, from the mold 1 and, if desired, also the step of removing the at least one insert 3a, if provided, from the bottom of the spacer device SD, or a part thereof. This step can be facilitated by the presence of a light or through opening 2e in the bottom 2d, since in this case the insert could be pressed from below through the light or through opening 2e, thereby facilitating the extraction of the spacer device SD from the molding cavity MC.

Clearly, if there is no light or through opening 2e, one could act in a different manner, for example by overturning the mold 1 and/or providing in advance a release material on the walls defining the molding cavity MC.

Finally, according to the method, the step of polishing or surface finishing or cutting of the forming burrs of the thus obtained spacer device SD or of a part thereof can also be provided.

At this point, if desired, it is possible to reuse the mold 1 (after cleaning the respective components) to obtain another spacer device SD with dimensions (heights or thicknesses)

equal to the one already obtained or even different, this being achieved by using different adjusting means.

In this regard, the surgeon, after obtaining a spacer device or a part thereof by means of the mold, could evaluate, for example by testing it on the patient, that this device or part is too large or too small, in which case would use the mold, acting on the adjusting means and/or on the reference means to obtain a spacer device or a part thereof with different dimensions, for example smaller or larger.

Moreover, it is evident that according to the adjusting means 3, thanks to a mold according to the present invention, it is possible to form at least two spacer devices SD with heights or thicknesses different with each other, according to the needs.

Clearly, with the expression in such a way that the mold 1 allows to form at least two spacer devices SD with different heights or thicknesses different with each other, it is meant that the mold, depending on the adjusting or reference means used, ensures the possibility of obtaining two or more different spacer devices SD. However, it will be understood that in the case of disposable mold, only one spacer is actually obtained thanks to the mold, but the surgeon or operator can decide, when the mold has not yet been used, which (with what thickness/height) spacer device SD is to be obtained.

Therefore, basically, in the case of a disposable mold, the mold can be used to make a single spacer device, but the height or thickness of this spacer device can be established in a certain range.

Thus, if a disposable mold is used, the same or the respective kit makes it possible to obtain a plurality of sizes of spacer device, but once the operator or the surgeon has established the one suitable for the implantation site, it is obtained, if desired using a specific adjusting means 3, a single spacer device corresponding to the desired size.

Moreover, it could be also possible to have a disposable mold in the sense of single patient, i.e., that it is not used for different patients and thus it has not to be re-sterilized every time, but the doctor or surgeon for the same patient can mold (as already partially indicated) more spacers or more parts/ thicknesses of a spacer device until the most suitable is identified according to the physical characteristics of the patient.

Therefore, the spacer device SD that can be obtained has a height that depends on the adjusting means used and/or the established reference means.

More particularly, the spacer device SD comprises a joint surface JS which can be established by a respective surface of the mold or also by the closure element SD1 pre-formed outside the mold 1 and therefore used in the latter during the respective method of obtaining of a spacer device SD.

The spacer device SD then includes a constraint or implant surface CS to a respective bone site, for example the tibial bone of the knee joint.

The spacer device SD is then provided with an intermediate section or thickness SD2 between the joint surface JS and the constraint or implant surface CS, for example between the closure element SD1 and the constraint or implant surface CS.

The height and, if desired, also the configuration of the intermediate section or thickness SD2 clearly varies according to the adjusting means 3 used, for example the insert 3*a* used or the reference means established.

With reference to the non-limiting embodiment illustrated in the figures, the intermediate section SD2 has an external configuration with steps, which are formed in the configuration of the defining or delimiting sections 4. Clearly, the intermediate section SD2 could also have an external surface which is not in steps, this according to the configuration of the molding cavity MC.

Of course, the spacer device SD can also have a stem SD3 protruding from the constraint surface CS, which stem SD3 can be obtained thanks to the hollow stem 3*c* of the insert 3*a*.

Figure 16:
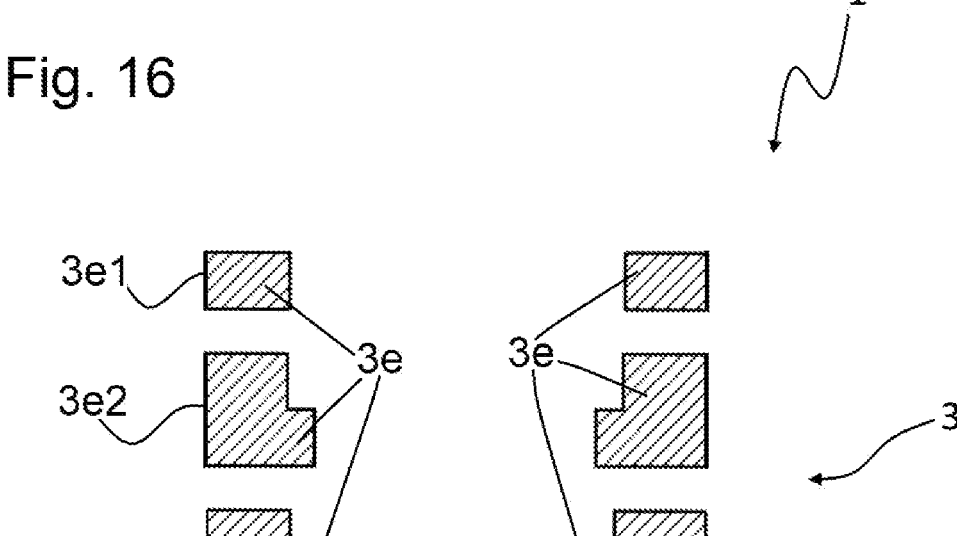
FIG. 16 is a schematic view of a first variant of mold and kit according to the present invention.
Figure 16:
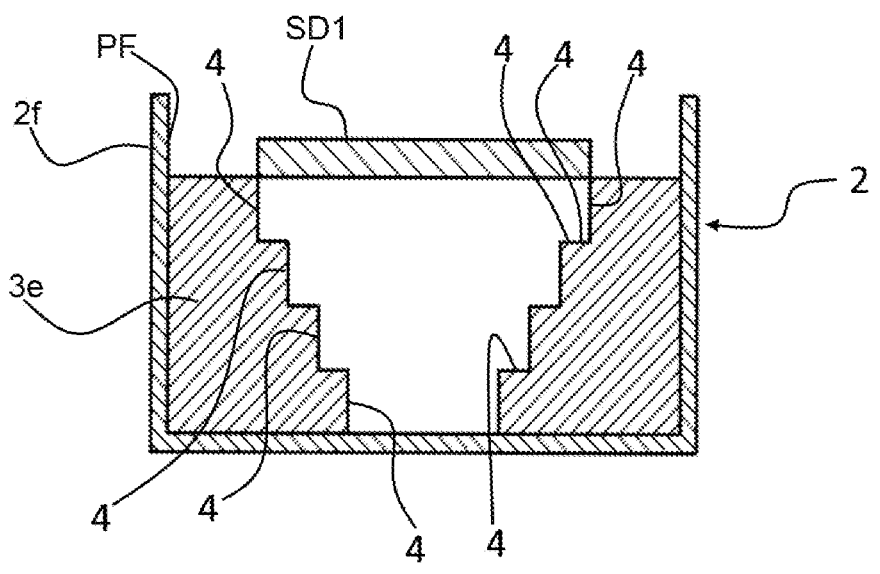

With reference now to the exemplary and non-limiting version of the invention shown in FIG. 16, the adjusting means 3 comprise at least one auxiliary component 3*e*, for example insertable or engageable or connectable with the main body 2 in such a way as to define the bottom and/or the top of the at least one molding cavity MC.

According to this variant, the main body 2 comprises a base wall 2*a* and a side wall 2*f*, for example annular or cylindrical extending from the edge of the base wall 2*a*. A positioning zone PZ for the auxiliary components 3*e* is defined between the base wall 2*a* and the side wall 2*f*.

In this case, the auxiliary components 3*e* can be configured as a ring defining internally a cylindrical surface or, if desired, also with two, three, four or more steps.

The molding cavity MC is defined in this case by the auxiliary component 3*e* or, better, by the area defined internally by the latter and the respective bottom by the base wall 2*a* or by an insert 3*a*. Therefore, actually, the auxiliary component 3*e* defines the lateral surface and the top of the molding cavity MC.

The kit 20 inherent to this variant thus comprises a main body 2 as well as two, three, four or more auxiliary components 3*e*. Such auxiliary components 3*e* would differ from each other in height. Thus, for example, a first annular auxiliary component 3*e*1 defining a cylindrical internal surface, a second annular auxiliary component 3*e*2 defining an internal surface for example with two steps, then a third 3*e*3 defining an internal surface for example with three steps and if desired, others, with the height of the first auxiliary component 3 lower than the second, which in turn has a height lower than the third and so on.

Naturally, the various auxiliary components 3*e* could also all be cylindrical, but with different heights from each other.

In this case, the defining or delimiting sections 4 would be defined by the auxiliary components 3*e*.

If desired, at least one insert 3*a* can also be provided to delimit the bottom of the mold and then facilitate the extraction of a spacer device SD after the same has been formed. In this case, clearly, the main body 2 would have a through hole in the respective base wall 2*a*.

The method of using such a mold is similar to that described above, but the step of defining or delimiting the desired height or thickness of the spacer device SD or of a part thereof by means of adjusting or reference means 3 involves inserting a specific auxiliary component 3*e* in the positioning area until it abuts against the bottom of the base wall 2*a*. Clearly the height of the spacer device SD would be defined as a function of the auxiliary component 3*e* chosen or rather the height of the latter.

Subsequently, a suitable material is cast into the molding cavity MC defined by the auxiliary component 3*e* until it reaches the top of the latter and, if necessary, a closure element SD1 is placed on the material before its polymerization and/or hardening. The closure element SD1 can have a width equal to the top of the molding cavity MC, in which case the closure element SD1 rests only on the cast or placed material or it rests externally or laterally on the top surface of the auxiliary component 3*e*.

If desired, before placing or casting the material into the molding cavity MC, an insert 3*a* is placed for defining and closing the bottom of the mold.

The other steps are similar to those indicated above for the embodiment of FIGS. 1 to 15.

Figure 17:
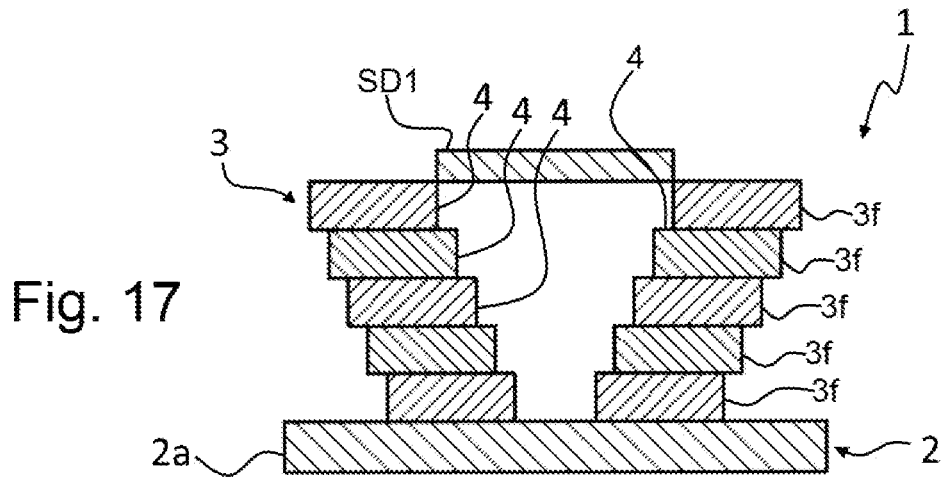
FIGS. 17 to 19 are schematic views of respective variants of the mold according to the present invention.

As regards the exemplary and non-limiting version of the invention shown in FIG. 17, the adjusting means 3 comprise at least one auxiliary component 3*f*, which for example can be rested on the main body 2.

In this case, the auxiliary components 3*f* can be configured as a ring, internally defining a cylindrical or even stepped surface.

According to this variant, to increase or decrease the height of the molding cavity MC, several auxiliary ring components 3*f* placed one on top of the other can be used.

In fact, therefore, the auxiliary component 3*f* defines the lateral surface and the top of the molding cavity MC.

The molding cavity MC is defined in this case by an auxiliary component 3*f* or by a plurality of auxiliary components 3*f* stacked and, if desired, by the bottom 3*d* of the main body 2 or by an insert 3*a* arranged on it.

Preferably, when several auxiliary components 3*f* are stacked, in the direction moving away from the base wall 2*a*, each auxiliary component 3*f* has a internal diameter smaller than the next and upper auxiliary component 3*f*.

Even in this case a closure element SD1 can be associated with the mold 1, for example with a width or section equal to or slightly smaller than the passage section of the internal surface of the auxiliary component 3*f* distal from the base wall 2*a*.

Figure 18:
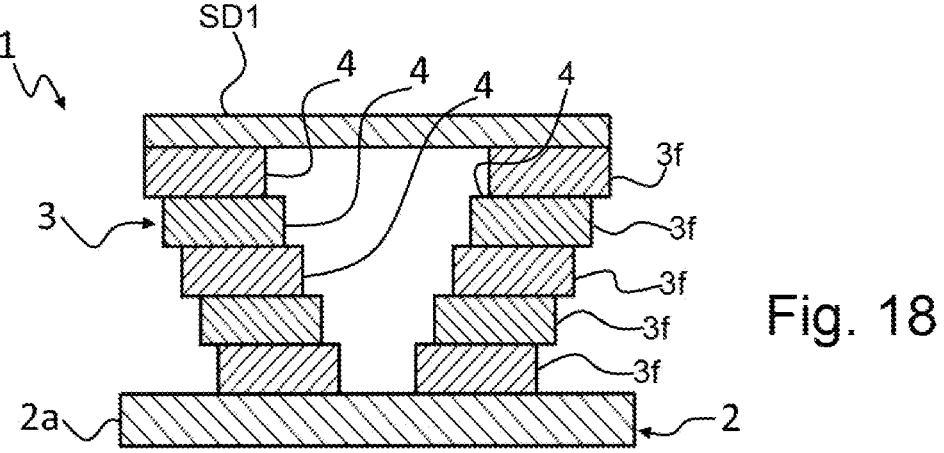

The embodiment of FIG. 18 is similar to that of FIG. 17, but with a closure element SD1 with width or section greater than the passage section of the internal surface of the auxiliary component 3*f* distal from the base wall 2*d*, so that the closure element SD1 can be placed on this auxiliary component.

Figure 19:
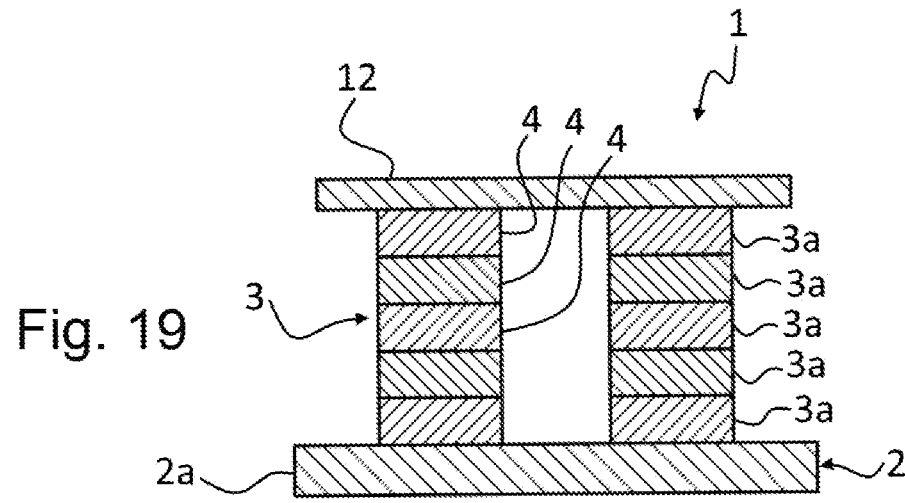

As regards the embodiment of FIG. 19, it is similar to that of FIGS. 17 and 18, but with auxiliary components 3*f* all annular with the same size.

The forming method by means of the molds of FIGS. 17 to 19 is similar to that described for the mold of FIG. 16.

Figure 20:
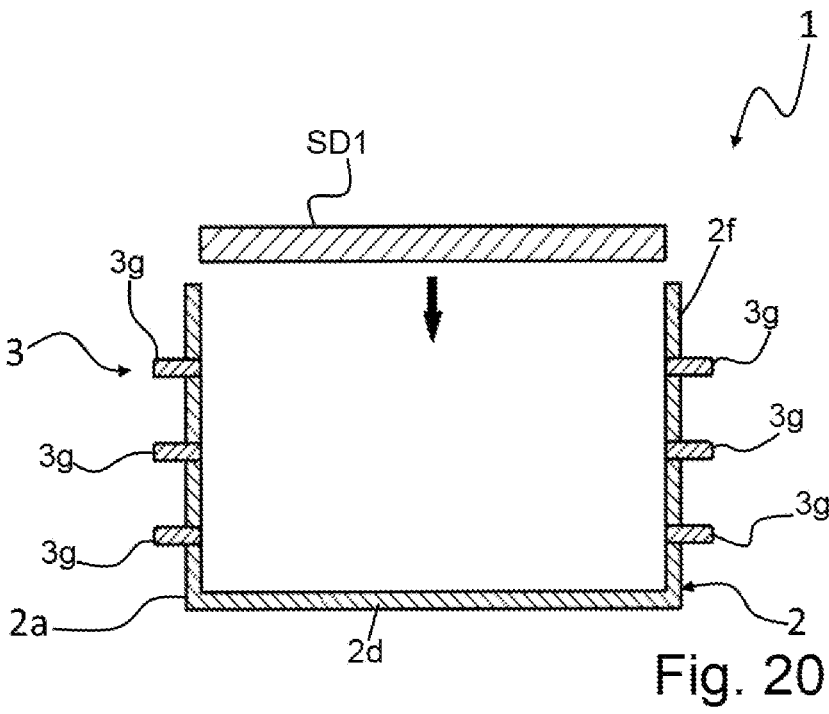
FIGS. 20 and 21 illustrate another mold according to the present invention in respective operational settings.
Figure 21:
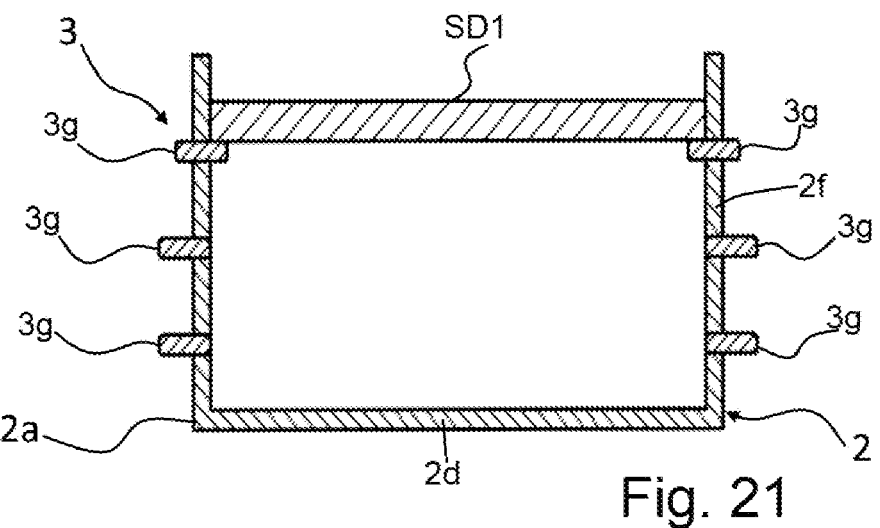

According to the exemplary and non-limiting version of the invention shown in FIGS. 20 and 21, the reference means 3 comprise one or more pins 3*g*, which can be engaged in the main body 2 in such a way as to define the top of the at least one molding cavity MC. In particular, the pin 3*g* can be, in use, fitted in the main body 2 in such a way as to constitute a reference for the controlled filling of at least one molding cavity.

According to this variant, the main body 2 comprises a base component 2*a* configured as a base wall and a side wall 2*f*, for example annular or cylindrical extending from the edge of the base wall 2*a*. The molding cavity MC is defined between the base wall 2*a* and the side wall 2*f*.

In this case, a plurality of pins 3*g* are provided which are fitted in the side wall 2*f* and can be moved between a rest position, outside the molding cavity MC and a working position in which the pins 3*g* are pressed through the side wall 2*f* up to protrude into the molding cavity MC.

According to the non-limiting embodiment illustrated in the figures, several pins are provided, two or more positioned or movable at a first level of the molding cavity MC, two or more positioned or movable to a second level of the molding cavity MC and, if desired, also pins 3*g* at a third, fourth or other level of the cavity MC.

With such a mold, the step of defining or delimiting, by means of adjusting or reference means 3, the desired height or thickness of the spacer device SD or in any case of a part thereof, involves establishing the filling level, which determines the height or thickness of the spacer device SD and then inserting the pins 3*g* corresponding to the desired filling level into the side wall 2*f*.

Subsequently, a special material is cast or placed in the molding cavity MC until reaching the top of the latter and then the pins 3*f* fitted.

Subsequently, if necessary, a closure element SD1 is placed on the material inserted or cast in the molding cavity MC, before its polymerization and/or hardening.

If desired, before placing or casting the material into the molding cavity MC, an insert 3*a* is placed for defining and closing the bottom of the mold.

As you will be able to ascertain, the mold 1, and in particular the kit 20, offers the possibility to customize the height or thickness of a spacer device SD at will, thus being able to adapt the latter to the particular needs of a patient.

The spacer device SD that can be obtained therefore has a height that depends on the adjusting means used and/or the established reference means.

The mold 1, and in particular the kit 20, is fast and easy to use and at the same time has also competitive costs for the production of the spacer devices SD.

It has thus been seen that the present invention fully achieves the proposed aims.

The mold 1, the kit 20 and the method described above are susceptible to numerous modifications and variations within the scope of protection of the following claims.

The invention claimed is:

1. A mold (1) for forming spacer devices (SD) or parts thereof for replacement of a joint prosthesis or of a part thereof, comprising:

a main body (2) defining at least one molding cavity (MC); and adjusting means for adjusting (3) a height of said at least one molding cavity (MC), so as to enable a variation of the height of said at least one molding cavity (MC) or to carry out a controlled filling of the at least one molding cavity in such a way that said mold (1) allows forming at least two spacer devices (SD) with different heights or thicknesses in relation to each other, wherein said main body (2) comprises a base component (2*a*), wherein said adjusting means (3) comprises at least one auxiliary component or insert (3*a*, 3*e*, 3*f*) engageable or connectable with said base component (2*a*), wherein said at least one auxiliary component or insert (3*a*, 3*e*, 3*f*) is designed to define a bottom and/or a top of said at least one molding cavity (MC), said base component (2*a*) comprising one or more defining or delimiting sections (4) configured as steps extending from an inner wall of said at least one molding cavity to engage said at least one auxiliary component or insert and arranged to define or delimit a lateral surface or extension of said at least one molding cavity (MC), or wherein said at least one auxiliary component or insert (3*e*, 3*f*) is configured as a ring defining internally a surface that is cylindrical or stepped in staircase manner, said at least one auxiliary component or insert (3*e*, 3*f*) comprising one or more defining or delimiting sections (4) that define or delimit the lateral surface or extension of said at least one molding cavity (MC), said at least one molding cavity (MC) being defined by said at least one auxiliary component or insert (3*e*) and at a bottom by said base component (2*a*) or by said at least one auxiliary component or insert (3*e*, 3*f*).

2. The mold (1) according to claim 1, wherein said one or more defining or delimiting sections (4) delimit at least one surface (4c) for contact or abutment of an auxiliary component or insert (3a).

3. The mold (1) according to claim 2, wherein said one or more defining or delimiting sections (4) delimit a plurality of contact or abutment surfaces (4c) for said auxiliary component or insert (3a), each contact or abutment surface (4c) being at a respective height of said molding cavity (MC).

4. The mold (1) according to claim 3, wherein said one or more defining or delimiting sections (4) delimit said at least one molding cavity (MC) configured in a staircase manner.

5. The mold (1) according to claim 1, wherein said main body (2) delimits at one end (2c) a main opening (MO) for accessing the at least one molding cavity (MC), and wherein said main body (2) comprises at least one bottom (2d) opposite to the main opening (MO).

6. The mold according to claim 1, further comprising reference means (3d) for a controlled filling of said at least one molding cavity (MC).

7. The mold according to claim 6, wherein said reference means comprise one or more reference projections, recesses, or notches (3d) extending upwardly from a contact or abutment surface (4c) towards an outside of the mold.

8. A kit (20) for forming at least two spacer devices (SD) or parts thereof for replacement of a joint prosthesis or of a part thereof, comprising:
   a mold (1) according to claim 1; and
   at least two auxiliary, lateral components, or inserts (3a) of different sizes from each other so as to allow a formation of the at least two spacer devices of different thicknesses or heights.

9. The kit (20) according to claim 8, wherein each of said at least two auxiliary, lateral components, or inserts (3a) has a base (3b) of a different width from the other insert or inserts, so that each insert (3a) is abuttable against a respective contact or abutment surface (4c) different from the other insert or inserts.

10. A method of obtaining or forming a spacer device (SD) or a part thereof, comprising the following steps:
   providing a mold (1) according to claim 1;
   defining or delimiting a desired height or thickness of said spacer device (SD) or the part thereof through said adjusting means (3);
   providing a material for making said spacer device (SD) or the part thereof;
   placing and/or casting said material in the at least one molding cavity (MC) of said mold (1) up to the height or the thickness of said spacer device (SD) or of the part thereof that was previously defined or delimited by said adjusting means (3);
   waiting for a time for a curing and/or hardening of said material and forming said spacer device (SD) or the part thereof;
   extracting said spacer device (SD) or the part thereof from the mold (1).

11. The method according to claim 10, wherein said step of defining or delimiting comprises a sub-step of inserting the insert (3a) until the insert abuts against an abutment or contact surface (4c) so as to constitute, with the insert (3a), a bottom of the at least one molding cavity (MC).

12. The method according to claim 10, further comprising a step of applying or abutting a closure element (SD1) on an upper, in use, surface of the material that was previously placed and/or casted in the mold (1), so that the closure element (SD1) constitutes a top of the spacer device (SD) or of the part to be formed.

13. The method according to claim 10, wherein the step of extracting comprises pressing the insert (3a) from below through a light or through opening (2e), thereby facilitating an extraction of the spacer device (SD) from the at least one molding cavity (MC).

14. A mold (1) for forming spacer devices (SD) or parts thereof for replacement of a joint prosthesis or of a part thereof, comprising:
   a main body (2) defining at least one molding cavity (MC); and
   adjusting means for adjusting (3) a height of said at least one molding cavity (MC), so as to enable a variation of the height of said at least one molding cavity (MC) or to carry out a controlled filling of the at least one molding cavity in such a way that said mold (1) allows forming at least two spacer devices (SD) with different heights or thicknesses in relation to each other,
   wherein said main body (2) comprises a base component (2a),
   wherein said adjusting means (3) comprise at least one auxiliary or lateral component or insert (3a, 3e, 3f) engageable or connectable with said base component (2a),
   wherein said at least one auxiliary or lateral component (3a, 3e, 3f) is designed to define a bottom of said at least one molding cavity (MC), or said at least one auxiliary or lateral component or insert (3a, 3e, 3f) is designed to define the bottom and/or a top of said at least one molding cavity (MC) and comprises one or more defining or delimiting sections (4) arranged to define or delimit a lateral surface or extension of said at least one molding cavity (MC),
   wherein said main body (2) delimits at one end (2c) a main opening (MO) for accessing the at least one molding cavity (MC), and wherein said main body (2) comprises at least one bottom (2d) opposite to the main opening (MO), and
   wherein said bottom (2d) of said main body is open so as to define a light or through opening (2e).

15. The mold (1) according to claim 14, wherein a cross-section of the molding cavity (MC) decreases from the main opening (MO) towards the bottom of the main body (2).

16. The mold according to claim 14, wherein said insert (3a) comprises at least one base (3b) and a hollow stem (3c) rising from the base (3b), said base (3b) defining an opening (3b 1) that opens into the hollow stem (3c) so as to allow a deposition of a material for forming a spacer device (SD) also in the hollow stem (3c) after the insert (3a) has been placed in or on the main body (2).

17. The mold according to claim 16, wherein an end of said hollow stem (3c) protrudes at the light or through opening (2e).

* * * * *